US011696680B2

United States Patent
Elson et al.

(10) Patent No.: US 11,696,680 B2
(45) Date of Patent: Jul. 11, 2023

(54) EAR EXAMINATION APPARATUS (71) Applicant: IP2IPO INNOVATIONS LIMITED, London (GB)

(72) Inventors: Daniel Stuart Elson, London (GB); Miroslav Janatka, London (GB); Taranjit Singh Tatla, London (GB); Arvind Singh, London (GB); Savram Krishan Ramdoo, London (GB)

(73) Assignee: IP2IPO Innovations Limited, London (GB)

( * ) Notice: Subject to any disclaimer, the term of this patent is extended or adjusted under 35 U.S.C. 154(b) by 338 days.

(21) Appl. No.: 16/772,445

(22) PCT Filed: Dec. 11, 2018

(86) PCT No.: PCT/GB2018/053594
§ 371 (c)(1),
(2) Date: Jun. 12, 2020

(87) PCT Pub. No.: WO2019/116024
PCT Pub. Date: Jun. 20, 2019

(65) Prior Publication Data
US 2021/0068645 A1 Mar. 11, 2021

(30) Foreign Application Priority Data
Dec. 13, 2017 (GB) .................................... 1720758

(51) Int. Cl.
*A61B 1/227* (2006.01)
*A61B 1/00* (2006.01)
(Continued)

(52) U.S. Cl.
CPC .......... *A61B 1/227* (2013.01); *A61B 1/00066* (2013.01); *A61B 1/00101* (2013.01);
(Continued)

(58) Field of Classification Search
CPC .................................. A61B 1/227; A61B 1/32
See application file for complete search history.

(56) References Cited

U.S. PATENT DOCUMENTS

| 2,797,684 A | 7/1957 | Moore |
| 3,224,437 A | 12/1965 | Hardgrove |

(Continued)

FOREIGN PATENT DOCUMENTS

| CN | 203786408 U | 8/2014 |
| CN | 204207710 U | 3/2015 |

(Continued)

OTHER PUBLICATIONS

Response to UK IPO Search and Examination Report #2. App. No. 1720758.0 (dated Dec. 10, 2019).
(Continued)

*Primary Examiner* — Eric S Gibson
(74) *Attorney, Agent, or Firm* — Foley & Lardner LLP (57) ABSTRACT

An ear examination tool comprises a handle and a speculum mount coupled to the handle. The speculum mount is configured for retaining a disposable speculum. An spacing element is coupled to the handle and extends from the handle. A smartphone mount is coupled to the spacing element, and the spacing element is configured to maintain an optical separation distance between the speculum mount and the smartphone mount. The tool enables a clear view of the ear canal while allowing access by, and manipulation of, a microsuction tool being inserted into the ear canal. The extensive optical and data processing functionality of a "smartphone" can be integrated at low cost into an ear examination tool to provide a substantially improved piece of equipment for assisting in ear examination and microsuction of the ear.

11 Claims, 5 Drawing Sheets (51) Int. Cl.
*A61B 1/04* (2006.01)
*A61B 1/32* (2006.01)
*A61B 5/00* (2006.01)
*A61B 17/34* (2006.01)

(52) U.S. Cl.
CPC .............. *A61B 1/042* (2013.01); *A61B 1/32* (2013.01); *A61B 5/6898* (2013.01); *A61B 17/3421* (2013.01)

(56) References Cited

U.S. PATENT DOCUMENTS

| | | | |
|---|---|---|---|
| 3,840,004 A | 10/1974 | Heine | |
| 3,848,587 A | 11/1974 | McDonald | |
| 4,006,738 A | 2/1977 | Moore et al. | |
| 4,295,153 A | 10/1981 | Gibson | |
| 4,380,998 A | 4/1983 | Kieffer et al. | |
| 5,852,512 A | 12/1998 | Chikazawa | |
| 5,907,434 A | 5/1999 | Sekine et al. | |
| 5,916,150 A | 6/1999 | Sillman | |
| 5,944,711 A | 8/1999 | Pender | |
| 6,213,938 B1 | 4/2001 | Cook | |
| 7,354,399 B2 | 4/2008 | Strom et al. | |
| 8,062,216 B2 | 11/2011 | Raghuprasad | |
| 8,248,702 B2 | 8/2012 | Hoffman et al. | |
| D672,317 S | 12/2012 | Jibiki | |
| 8,587,498 B2 | 11/2013 | Connor | |
| 8,613,735 B2 | 12/2013 | Umeda et al. | |
| 8,908,015 B2 | 12/2014 | Filo et al. | |
| 9,097,902 B2 | 8/2015 | Conley | |
| 9,119,744 B2 | 9/2015 | Wellen et al. | |
| 9,137,517 B2 | 9/2015 | Geris et al. | |
| 9,176,325 B2 | 11/2015 | Lyons | |
| 10,463,307 B2* | 11/2019 | Sayani ................. A61B 5/0077 |
| 11,234,597 B1* | 2/2022 | Farr ..................... H04N 5/2256 |
| 11,324,452 B2* | 5/2022 | Sayani ..................... A61B 3/14 |
| 2002/0033200 A1 | 3/2002 | Alex et al. | |
| 2006/0055773 A1 | 3/2006 | Kutka | |
| 2010/0194860 A1 | 8/2010 | Mentz et al. | |
| 2012/0026298 A1 | 2/2012 | Filo et al. | |
| 2012/0245422 A1* | 9/2012 | Hasbun ................. G06F 1/1656 600/200 |
| 2012/0320340 A1* | 12/2012 | Coleman, III ........... A61B 3/10 351/208 |
| 2013/0023914 A1* | 1/2013 | Truong ................. A61B 1/0607 606/162 |
| 2014/0153091 A1 | 6/2014 | Boudreau et al. | |
| 2014/0218478 A1 | 8/2014 | Lang et al. | |
| 2014/0267637 A1 | 9/2014 | Hoberman et al. | |
| 2015/0087926 A1* | 3/2015 | Raz ....................... G16H 50/20 600/301 |
| 2015/0103146 A1 | 4/2015 | Rose et al. | |
| 2015/0217041 A1 | 8/2015 | Monty et al. | |
| 2015/0234189 A1 | 8/2015 | Lyons | |
| 2015/0234192 A1 | 8/2015 | Lyons | |
| 2015/0253574 A1 | 9/2015 | Thurber | |
| 2016/0249805 A1* | 9/2016 | Salvati ..................... A61B 3/12 351/206 |
| 2016/0267712 A1 | 9/2016 | Nartker et al. | |
| 2016/0349509 A1 | 12/2016 | Lanier et al. | |
| 2017/0303857 A1* | 10/2017 | Perkins .............. A61B 1/00052 |
| 2019/0216402 A1* | 7/2019 | Sayani ..................... A61B 3/13 |
| 2020/0060623 A1* | 2/2020 | Sayani ..................... A61B 5/441 |
| 2021/0068645 A1* | 3/2021 | Elson ..................... A61B 1/32 |
| 2021/0128066 A1* | 5/2021 | Sayani .............. A61B 1/00016 |
| 2022/0000342 A1* | 1/2022 | Knecht .................. G03B 17/14 |
| 2022/0133141 A1* | 5/2022 | Mock ................. A61B 1/00048 348/77 |
| 2022/0233065 A1* | 7/2022 | Babson .............. A61B 1/00032 |
| 2022/0233148 A1* | 7/2022 | Knecht .................. A61B 1/227 |
| 2022/0240771 A1* | 8/2022 | Domecus ............... A61B 1/227 |
| 2022/0257197 A1* | 8/2022 | Sayani ................. A61B 5/6898 |

FOREIGN PATENT DOCUMENTS

| | | | |
|---|---|---|---|
| CN | 207249239 U | 4/2018 | |
| EP | 1 262 205 | 12/2002 | |
| EP | 2 299 728 | 3/2011 | |
| EP | 2 730 963 | 5/2014 | |
| EP | 2789290 A1 * | 10/2014 | ............. A45C 11/00 |
| ES | 1118480 U | 8/2014 | |
| FR | 3004098 A1 * | 10/2014 | ............. A45C 11/00 |
| GB | 2 522 401 | 7/2015 | |
| GB | 2 562 901 A | 11/2018 | |
| JP | 3542397 B2 | 10/1996 | |
| KR | 20130049704 A | 5/2013 | |
| KR | 101697459 | 1/2017 | |
| WO | WO-01/75505 | 10/2001 | |
| WO | WO-2012/035174 | 3/2012 | |
| WO | WO-2012/058641 | 5/2012 | |
| WO | WO-2013156999 A1 * | 10/2013 | ............. A61B 1/227 |
| WO | WO-2015/035229 | 3/2015 | |
| WO | WO-2015/173444 | 11/2015 | |
| WO | WO-2018/197870 A1 | 11/2018 | |
| WO | WO-2019116024 A1 * | 6/2019 | ......... A61B 1/00066 |
| WO | WO-2021011855 A1 * | 1/2021 | ......... A61B 1/00045 |
| WO | WO-2022006369 A1 * | 1/2022 | ......... A61B 1/00045 |
| WO | WO-2022094633 A1 * | 5/2022 | ............... A61B 1/06 |
| WO | WO-2022165115 A1 * | 8/2022 | ............. A61B 1/227 |

OTHER PUBLICATIONS

Response to UK IPO Combined Search and Examination Report #1, App. No. 1720758.0 (dated Oct. 10, 2019).
UK IPO Combined Search and Examination Report #1, App. No. 1720758.0 (dated May 11, 2018).
UK IPO Search and Examination Report #2, App. No. 1720758.0 (dated Oct. 31, 2019).
UK IPO Third Party Observations, App. No. 1720758.0 (dated Jan. 28, 2020).
Office Action issued in EP Application No. 18826781.9 dated Sep. 23, 2022.
International Search Report and Written Opinion, PCT/GB2018/053594, Imperial Innovations Limited (dated May 8, 2019).

* cited by examiner

EAR EXAMINATION APPARATUS

CROSS-REFERENCE TO RELATED APPLICATIONS

This application is a National Stage Application of PCT/GB2018/053594, filed Dec. 11, 2018, which claims the benefit of and priority to Great Britain Patent Application No. 1720758.0, filed Dec. 13, 2017, the entire contents of both of which are incorporated herein by reference.

TECHNICAL FIELD

This disclosure relates to ear examination apparatus and to apparatus for the removal of ear wax or other obstructions in the ear.

BACKGROUND

Current provisions for professional removal of ear wax include ear irrigation/syringing, ear microsuction and aural toileting. Syringing is a relatively crude technique with recognised safety hazards, requiring water to be delivered under pressure to dislodge wax. Ear irrigation works by using an electronic ear irrigator, which involves a variable pressurised flow of water into the ear canal to remove the wax. The water is at body temperature and intermittent review with an otoscope is required to ensure complete wax removal. This is widely used in General Practices by trained healthcare professionals and is generally thought to be safe and pain free but there are contra-indications to the procedure, for example a history of perforation, ear discharge, previous ear surgery and severe tinnitus. In some cases, irrigation can lead to an otitis externa due to residual water in the ear canal as well as canal and tympanic membrane trauma and even perforation as well as significant pain to the patient. Irrigation is typically performed without direct vision of the ear canal and therefore there is potential for harm.

If ear irrigation is unsuccessful a referral to an ENT specialist is generally required in order to perform ear microsuction and aural toileting. Ear microsuction may be performed using a binocular operating microscope allowing for illuminated stereoscopic vision and magnification into the ear canal. Removal of wax occurs by suction at low pressures. The ability to visualise the ear canal ensures that the sensitive ear canal wall is not touched, making the process more comfortable and less traumatic. If the wax is very hard then aural toileting can be performed using specialist equipment such as a Jobson-Horne Probe or wax hook, again under direct vision.

Compared to ear irrigation, microsuction is safer, quicker, better tolerated and has fewer complications, but the apparatus for performing microsuction is generally more complex and expensive and microsuction and aural toileting are most commonly performed in a hospital environment.

SUMMARY

It is an object of the invention to provide apparatus to enable the more widespread deployment of ear microsuction techniques, for example by providing a suitable low cost, easily used viewing platform for providing images of the ear canal during irrigation and/or microsuction.

According to one aspect, the present invention provides an ear examination tool comprising:
a handle;
a speculum mount coupled to the handle, the speculum mount configured for retaining a speculum;
a spacing element coupled to the handle and extending from the handle;
a smartphone mount coupled to the spacing element,
the spacing element configured to maintain an optical separation distance between the speculum mount and the smartphone mount.

The speculum mount coupled to the handle may extend in a first direction from the handle and the spacing element may extend in a second direction from the handle. The second direction may be generally opposite to the first direction. The spacing element may be configured to maintain the optical separation distance between the speculum mount and the smartphone mount along an axis aligned with the first and second directions. The spacing element and smartphone mount may be configured to provide an optical path from the smartphone mount to and along an axis of the speculum mount. The speculum mount, the spacing element and the smartphone mount may be configured to provide an optical path from the smartphone mount to and along an axis of the speculum mount, while allowing a clear space for access into and through a speculum when mounted to the speculum mount, from a position between the speculum mount and the smartphone mount and at an oblique angle to the optical axis. The smartphone mount may comprise a cradle configured to releasably receive and retain a smartphone. The cradle may include at least one aperture therein positioned such that, when a smartphone is mounted in the cradle, the ear examination tool provides a first optical path extending from a first position of the smartphone mount corresponding to a smartphone camera to and along an axis of the speculum mount, and a second optical path extending from a second position of the smartphone mount corresponding to a smartphone light source and oblique to the axis of the speculum mount. The first and second optical paths may intersect at a point distal of the speculum mount. The speculum mount may comprise an aperture extending therethrough and a receptacle on a distal side of the speculum mount for attachment of a speculum. The handle may extend in a direction orthogonal to the first and second directions and in which the handle is positioned less than 3 cm (e.g. approximately 2 cm) from a distal side of the speculum mount along the axis. The smartphone mount may further comprise an optical element configured, in use, to be positioned over a camera of a smartphone when installed in the smartphone mount. The smartphone mount may further comprise an optical element configured, in use, to be positioned over a light source of a smartphone when installed in the smartphone mount. The optical element may comprise a stereoscopic vision element configured to provide dual images to a smartphone camera when the smartphone is installed in the smartphone mount. The smartphone mount may be adaptable to fit a plurality of different types of smartphone. The ear examination tool may comprise a plurality of interchangeable smartphone mounts each configured to fit a different type of smartphone and each separately couplable to the spacing element. The handle may incorporate a fluid reservoir for supplying fluid to an ear suction apparatus. The handle may comprise a control trigger to implement a function in an associated suction device or an associated smartphone.

According to another aspect, the present invention provides a cannula grip/guide comprising:
a cannula retention shaft for receiving a cannula along an axis of the shaft;

a handgrip portion curving away from the axis of the cannula retention shaft and including a delivery tube retaining feature at a proximal end of the handgrip, laterally offset from the axis of the cannula retention shaft.

The delivery tube retaining feature may comprise a collar for receiving a delivery tube therethrough. The cannula grip/guide may further include a lateral lumen and lateral lumen connector extending radially outward from the shaft axis in a direction which is substantially opposite to the radial direction in which the handgrip portion diverges from the shaft axis. The cannula grip/guide may further include a cannula installed within the cannula retention shaft.

BRIEF DESCRIPTION OF THE FIGURES

Embodiments of the present invention will now be described by way of example and with reference to the accompanying drawings in which.

DETAILED DESCRIPTION

An important consideration in the design of an ear examination apparatus for use when performing microsuction is the ability to provide a clearest possible view of the ear canal while simultaneously allowing access by, and manipulation of, a microsuction tool being inserted into the ear canal. Another consideration is the ease with which a clinician or other medical professional may deploy both a visualisation apparatus for providing a view of the ear canal and the microsuction tool using the clinician's two available hands. Thus, it is desirable to provide apparatus which can de-skill or simplify the operation, i.e., to make the task easier.

In the present invention, it has been recognised that the extensive functionality of the ubiquitous modern "smartphone" offers a very low cost, light-weight and readily available set of advanced optical and data processing functions which can be integrated at low cost into an ear examination tool to provide a clinician or other medical professional with a substantially improved piece of equipment for assisting in ear examination and microsuction of the ear. The expression "smartphone" as used herein is intended to encompass all mobile telecommunication devices incorporating a suitable camera or other optical imaging element, digital data processing functions and display for displaying images.

Figure 1:
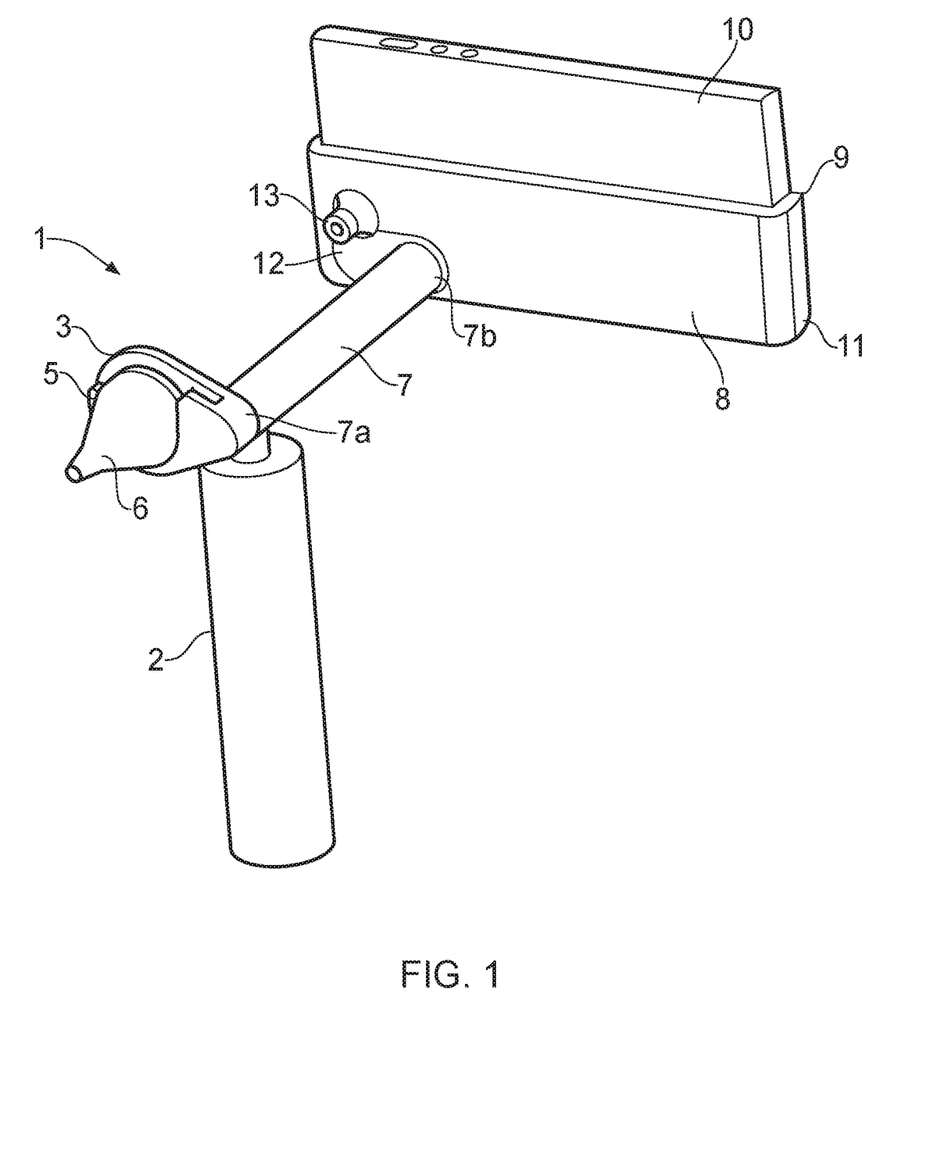
FIG. 1 shows a perspective, distal end schematic view of an ear examination tool.
Figure 2:
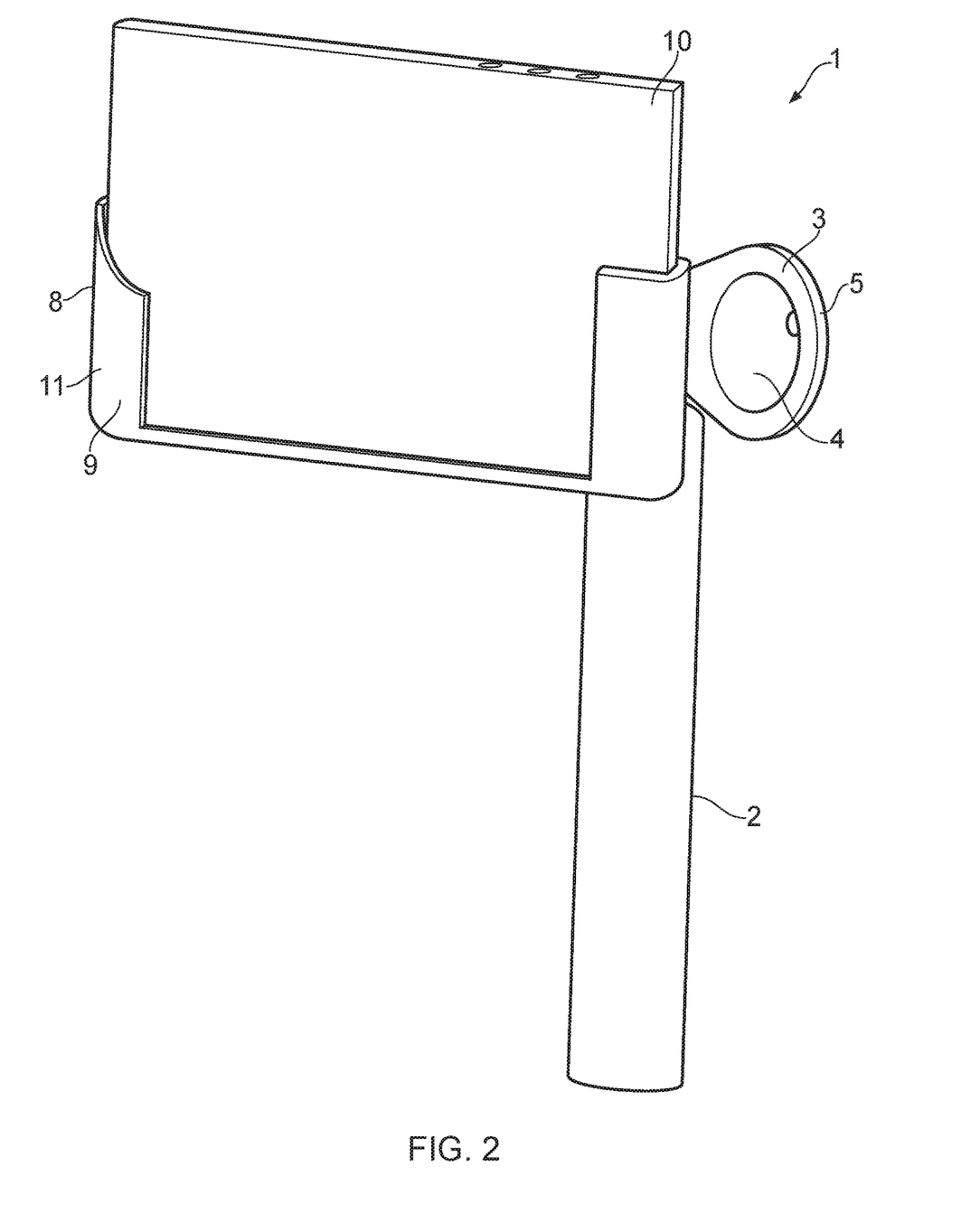
FIG. 2 shows a perspective, proximal end schematic view of the ear examination tool of FIG. 1.

With reference to FIGS. 1 and 2 there is shown an ear examination tool 1 comprising a handle 2 and a speculum mount 3 coupled to the handle 2. The speculum mount 3 defines an aperture 4 (visible in FIG. 2) extending through the mount 3 and a receptacle 5 configured to receive and engage a removeable speculum 6. The speculum mount 3 receives and retains the speculum 6 by way of a slide-in fitting, a bayonet-type fitting, a screw-thread fitting or any other arrangement suitable for attaching and detaching disposable specula. A Luer-type fitting is one possibility. The speculum mount 3 may be of a universal type adapted to receive different sizes and/or types of specula.

Also coupled to the handle 2 is a spacing element 7 which extends away from the handle 2 in a generally opposite direction to the direction of the speculum 6, to a smartphone mount 8. The near end of the ear examination tool 1 as viewed in FIG. 1 will be referred to as the distal end (i.e. the end that is presented furthest from the user/clinician and therefore closest to the patient) and the near end of the ear examination tool 1 as viewed in FIG. 2 will be referred to as the proximal end (i.e. the end that is closest to, and presented facing, the user/clinician). The spacing element 7 extends from its distal end 7a at the speculum mount 5 to its proximal end 7b at the smartphone mount 8, and serves to maintain an optical separation distance between the speculum mount 3 and the smartphone mount 8. The spacing element 7 may therefore be considered as an optical spacing element for reasons discussed later.

The smartphone mount 8 comprises a cradle 9 which is configured to releasably receive and retain a smartphone 10. In the example shown in FIG. 2, the cradle 9 provides a proximal side which exposes a substantial part of, and preferably all of, a display screen on the smart phone 10 while providing a suitable retention profile such as rim 11 to retain the edges and display face of the smartphone 10. The distal side of the cradle 9 (FIG. 1) includes at least one optical aperture 12 positioned such that, when the smartphone 10 is mounted in the cradle 9 as shown, a camera in the smartphone is exposed. The distal side of the cradle 9 preferably also includes at least one optical aperture 13 positioned such that, when the smartphone 10 is mounted in the cradle 9 as shown, a light source of the smartphone is exposed. The light source may be a flashlight of the smartphone. The optical apertures 12, 13 could each comprise a simple physical aperture in the cradle 9 or a shared single aperture, e.g. when the focussing and directionality of the camera lens and flashlight lens of the smartphone are being relied upon. Alternatively the optical aperture 12, 13 or apertures could comprise one or more optical elements to provide further optical processing such as focussing, magnification, optical path splitting or other features to be described later.

Figure 5:
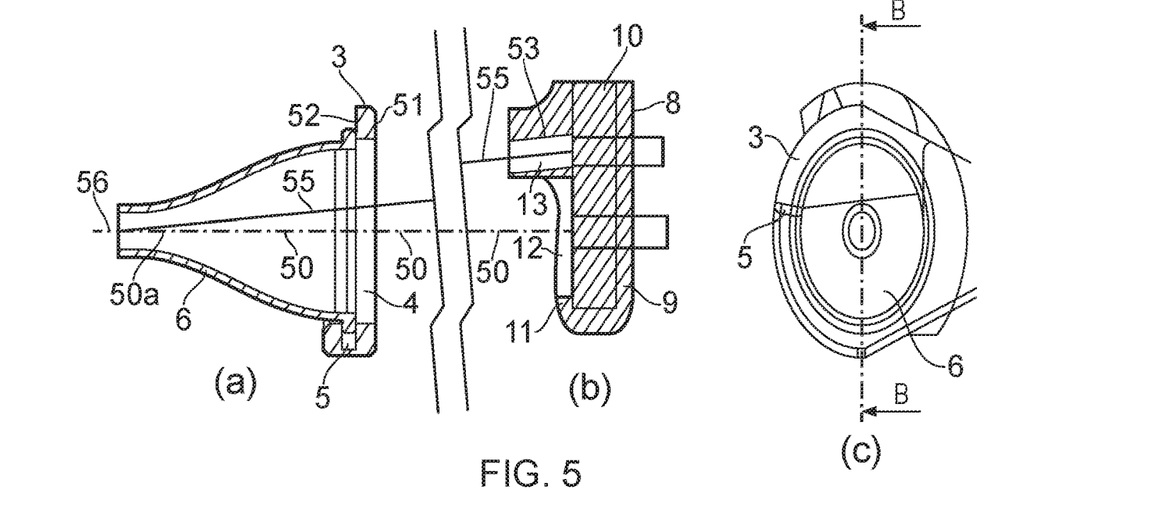
FIG. 5 shows (a) a cross-sectional side view and (c) a distal end view of a speculum holder, with speculum attached, of the ear examination tool of FIG. 1 or FIG. 3; and (b) a cross-sectional side view of a portion of a smartphone mount of the ear examination tool of FIG. 1 or FIG. 3.

With reference also to FIG. 5, the ear examination tool 1 thereby provides a first optical path 50 extending from a first position corresponding to the optical aperture 12 and the smartphone camera to and along an optical axis 50a corresponding to a central axis of the speculum 6 and the speculum mount 3. The optical axis 50a of the speculum mount 3 can be considered as the central orthogonal axis extending through the aperture 4 and between a proximal face 51 and a distal face 52 of the speculum mount, and extending through the speculum 6 when it is attached.

The ear examination tool 1 further provides a second optical path 55 extending from a second position (corresponding to the optical aperture 13 and the smartphone 10 flashlight) to the speculum 6 and the speculum mount 3, wherein the second optical path 55 is oblique to the first optical path 50, and the first and second optical paths intersect at a point 56 distal of the speculum mount 3.

With further reference to FIGS. 1 and 2, in one example the handle 2 extends in a direction generally orthogonal to the direction of the optical axis 50, and thus also orthogonal to the optical axis 50a of the speculum mount 3, and may be generally orthogonal to the axis of the spacing element 7.

In one example, the handle 2 is positioned less than approximately 3 cm along the optical axis 50 from the distal face 52 of the speculum mount 3. This arrangement provides an additional safety feature in that a user of the ear examination tool 1 may grip the handle 2 by way of a closed fist around the handle such that the user's fingers extend around the distal side of the handle 2. This means that when the speculum 6 is inserted into a patient's ear, the fingers and/or the knuckles of the user will tend to come into contact with the head of the patient and prevent accidental over-insertion of the speculum which might otherwise arise as a result of, for example, unintentional or involuntary movement of the patient or the user.

As shown in FIG. 5b, the optical aperture 12 may be a simple aperture for the smartphone camera to view through, and the optical aperture 13 may be an optical aperture comprising an optical element in the form of a light reflecting surface or light guiding surface and/or a light focussing path, e.g. incorporating a lens (not shown). The optical element may be configured to focus or guide light towards the intersection point 56 taking into account the length of the spacing element 7 and the offset of the optical aperture 13 from the first optical path 50.

Figure 3:
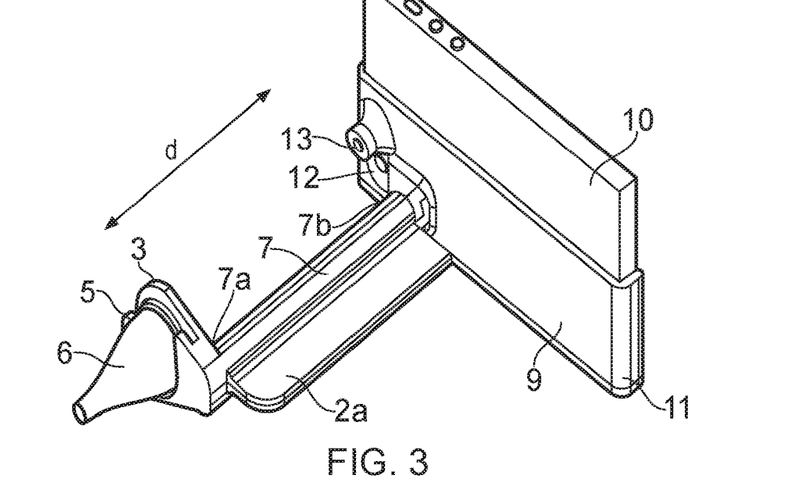
FIG. 3 shows a perspective view from above the distal end of another configuration of an ear examination tool.
Figure 4:
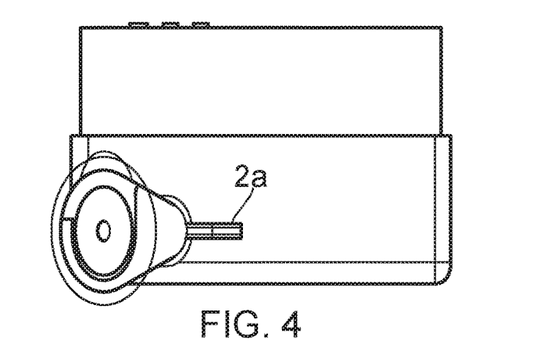
FIG. 4 shows a distal end view of the ear examination tool of FIG. 3.

An alternative form of ear examination tool 30 is seen in FIGS. 3 and 4. This arrangement may include common features to those described in connection with FIGS. 1, 2 and 5, but with a handle 2a that extends along the spacing element 7 thereby providing a different orientation of grip while still allowing a user good control of position and resistance against rotation of the tool 1 about the optical axis 50.

A purpose of the spacing element 7 is to provide a functional separation distance between the speculum 6 and the smartphone camera so that correct focussing of the smartphone camera through the speculum to a point 56 distal of the speculum 6 is achieved and readily controllable, and to ensure that the correct "line-of-sight" from the camera to the focal point distal of the speculum 6 is achieved.

Another purpose of the spacing element 7 is to enable sufficient separation or "free-space path" between the speculum mount aperture 4 and the smartphone mount 8 so that the user has a clear space by which to insert a microsuction apparatus cannula into the ear via the aperture 4 of the speculum mount 3 and thereby into and through the speculum 6, using the free hand not holding the handle 2 of the ear examination tool 1. It is important that the line of sight from the smartphone camera to and through the speculum 6 is maintained while the user introduces a microsuction device at a somewhat oblique angle to the optical axis 50a and into the ear via the aperture 4 and speculum 6. It is desirable that the user can easily direct and converge a distal end of a microsuction probe to the intersection point 56 distal of the speculum 6.

Figure 6:
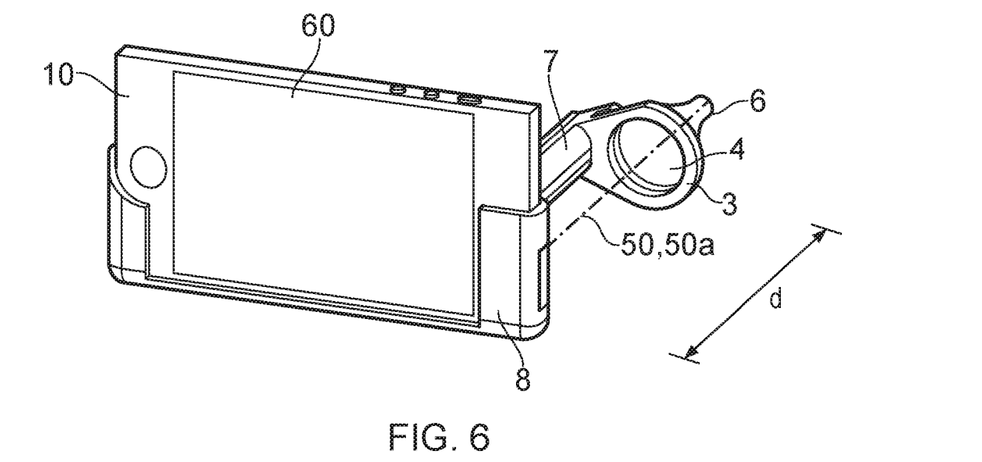
FIG. 6 shows a perspective proximal end view of the ear examination tool of FIG. 3.

This is best visualised with reference to FIG. 6, which shows the user's perspective view of the proximal end of the ear examination tool 1, with a smartphone 10 installed. The spacing element 7 and the smartphone mount 8 are disposed, in this arrangement, mainly to the left of the optical path 50/optical axis 50a with only the end of the smartphone which houses the camera and the speculum mount 3 itself overlying the optical axis 50a so that the user has a free space path of length d accessible from the right to introduce a microsuction apparatus cannula (or other instrument, if required) at a shallow angle through the aperture 4. The ear examination tool 1 can be gripped using the handle 2 (not shown in FIG. 6) with the left hand so that the right hand is available for manipulation of the microsuction cannula with the right hand.

The free space path of length 'd' between the smartphone mount 8 and speculum mount 3 is correspondingly found in the embodiment of FIGS. 1 and 2, best viewed from the perspective of FIG. 2, also providing the user with a clear space by which to insert a microsuction apparatus cannula into the ear via the aperture 4 of the speculum mount 3 and thereby into and through the speculum 6.

In a general aspect, the speculum mount 3, the spacing element 7 and the smartphone mount 8 are configured to provide an optical path 50 from the smartphone mount 8 to and along an axis of the speculum mount 3, while allowing a clear space for access into and through a speculum 6 when mounted to the speculum mount 3, from a position between the speculum mount 3 and the smartphone mount 8 and at an oblique angle to the optical axis 50a.

In preferred arrangements, the aperture 4 may have a diameter of between 7 and 10 mm to allow access of both the light path and a microsuction cannula into the speculum 6 which has a similar internal diameter opening. In some preferred arrangements, the distance d between the aperture 4 and the smartphone mount 8 lies in the range 6 to 10 cm to provide sufficient free space path for the user for access with a cannula. In one arrangement, the distance from the smartphone mount 8 to the speculum mount 3 is approximately 8 cm. An exemplary speculum 6 may have a cone shape arising from a large diameter 7.5 mm×8.5 mm tapering down to a small diameter 3 mm×4 mm, thereby allowing access to a microsuction cannula via the free space path length d at an angle of less than about 15 degrees, or less than 20 degrees or less than 30 degrees. The speculum cone shape may therefore have an angle between 15 and 30 degrees, the illustrated embodiment being approximately 15-20 degrees.

It is envisaged that the ear examination tool 1 can be provided as both left- and right-hand versions so that a user may always use a preferred or dominant hand for operation of the microsuction cannula and the other hand for holding the ear examination tool 1. Alternatively, the ear examination tool may be configured as a reversible tool, e.g. rotatable through 180 degrees about the optical axis 50a with consequent repositioning or rotating of the handle 2 around the spacing element 7 as required so that it still depends downwardly from the spacing element 7. Provision may also be made for reversal of the smartphone mount if necessary (this may depend on the type of clip or phone retaining mechanism in use, e.g. whether the smartphone mount is suitable for retaining a smartphone at any orientation without risk of the smartphone dropping out).

The smartphone 10 may be adapted, with suitable application software ('app'), to provide on its screen 60 (FIG. 6) a magnified and well-illuminated image of the inside of an ear canal into which the speculum 6 has been introduced. This can be achieved using the smartphone camera, and the smartphone flashlight, with suitable app control ensuring focussing in the appropriate place, e.g. at the intersection point 56. In some arrangements, the smartphone mount 8 may incorporate an additional optical element such as a lens (not shown) for increased optical magnification, and/or a further optical element for flashlight focussing on the intersection 56. In some arrangements, a suitable digital zoom/magnification may be provided by the phone app with or without requiring additional optical elements.

For improved flexibility, the ear examination tool may be provided as a kit of parts including a number of different smartphone mounts 8 all separately attachable to the spacing element 7, each configured to fit a different brand and/or model of smartphone.

Alternatively, the smartphone mount 8 may be of a 'universal' type adaptable by adjustment to fit a number of different brands and/or models of smartphone.

Figure 8:
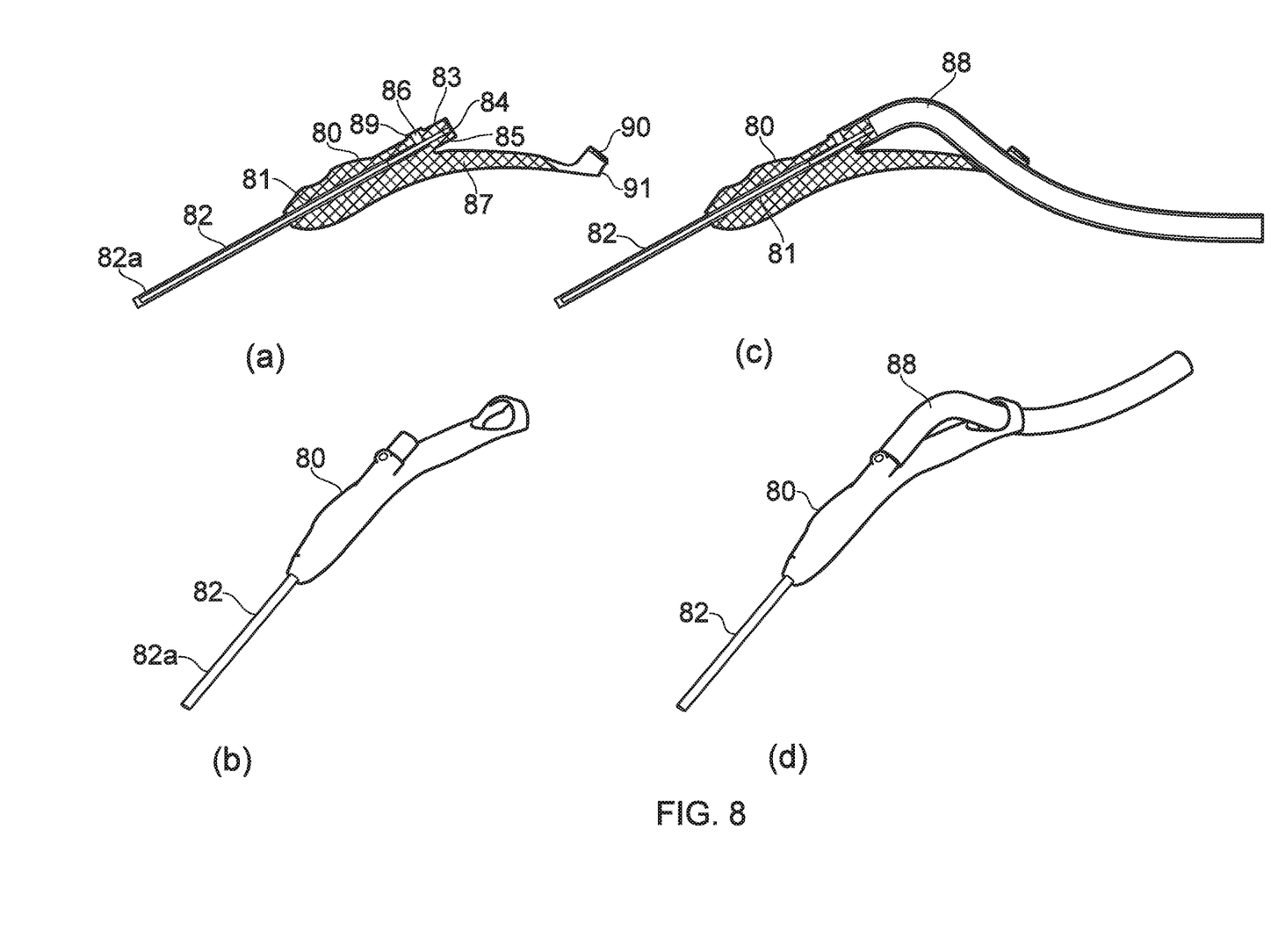
FIG. 8 shows (a) a cross-sectional side view and (b) a perspective view of a cannula grip and guide unit; and shows (c) a cross-sectional side view and (d) a perspective view of the cannula grip and guide unit with a flexible suction pipe attached.

Although the ear examination tool 1 may be used in conjunction with any suitable cannula or other instrument for insertion into the ear via the aperture 4, using the free space path d alongside the spacing element 7, an exemplary cannula arrangement for providing microsuction is shown in FIG. 8.

With reference to FIG. 8, a cannula grip or guide 80 has a cannula retention shaft 81 which is configured to receive a cannula 82 therethrough along an axis of the retention shaft. A distal end 82a of the cannula 82 extends beyond the end of the cannula grip 80 and also extends through the cannula grip 80 to a proximal portion 83. At the proximal portion 83 the grip 80 provides an axial lumen 84 extending proximally from the grip 80 and a lateral lumen 86 extending radially outward from the grip 80 axis. The axial lumen 84 is in fluid communication with a central lumen of the cannula 82 and the lateral lumen 86 is in fluid communication with a peripheral lumen of the cannula 82. The cannula grip 80 provides an axial lumen connector 85 for coupling a flexible delivery tube 88 thereto, and a lateral lumen connector 89 for coupling a flexible delivery tube (not shown) thereto. Any suitable connector type may be deployed.

A handgrip portion 87 of the grip 80 extends or diverges laterally away from the axis of the cannula retention shaft 81 and provides a curved handgrip which is particularly useful for holding the cannula in a pen-like grip for easy manipulation of the cannula 82 into a patient's ear through the aperture 4 of the ear examination tool 1 while presenting the cannula at a slightly oblique angle to the optical axis 50a. This may be further assisted by use of a cannula 82 which has a shallow angle bend (e.g. between 10 and 30 degrees) at some point along its length before the distal end 82a. For example, the cannula may have a length extending from the retention shaft 81 of between 8 and 10 cm and the bend may be located between 3 and 6 cm from the distal end 82a.

The handgrip portion 87 includes a delivery tube retaining feature, such as a loop 90 disposed at the proximal end 91 of the handgrip portion 87 which assists in guiding the delivery tube 88 away from the user's hand and away from the optical axis 50a when in use with the ear examination tool 1.

In the arrangement shown in FIG. 8, the delivery tube retaining feature is a closed loop 90 through which the delivery tube 88 may be passed before connecting its end to the connector 85. In other arrangements, any delivery tube retaining feature could be used such as an open clip into which the tube may be pressed laterally and retained by friction fit or by spring fingers, for example.

The lateral lumen connector 89 may be connected to a fluid source, e.g. a water source, for pumping water through the peripheral lumen of the cannula 82 and the axial lumen connector 85 may be connected to a suction source for sucking fluid (e.g. water and dislodged wax) through the central lumen of the cannula 82. In the preferred arrangement shown, the lateral lumen 86 and lateral lumen connector 89 extend in a radial direction substantially opposite (e.g. 180 degrees±45 degrees) to the radial direction in which the handgrip portion 87 of the grip 80 extends or diverges laterally away from the axis of the cannula retention shaft 81.

The cannula 82 is preferably a hydroplaning cannula providing for wax removal by fluid abrasion. In such an arrangement, fluid is delivered via the peripheral lumen of the cannula 82. The central lumen of the cannula 82 is slightly shorter than the peripheral lumen (e.g. by approximately 4 mm, or between 2 mm and 5 mm). As fluid is delivered from the distal end of the peripheral lumen, it is sucked radially inwards by suction provided at the distal end of the central lumen, thereby providing a shearing flow of fluid at the end of the cannula to abrade and/or otherwise dislodge wax at the distal end 82a of the cannula 82 and extract the wax via the central lumen.

The cannula 82 and grip/guide 80 may be provided as a unitary construction and as a disposable item. Alternatively, the cannula 82 may be provided as a separate part which can be installed in the grip 80 as the time of use. In such a case, the cannula 82 may be disposable whereas the grip 80 need not be.

Any suitable microsuction apparatus may be used in conjunction with the cannula 82 and in conjunction with the ear examination tool 1. A suction and fluid delivery device (not shown) can be coupled to the cannula 82 and the cannula can be fed into the ear canal under vision from the smartphone camera, to suck out ear wax. The preferred cannula 82, or suction probe, has a dual lumen arrangement that allows water to irrigate a target area whilst the suction is activated, sucking up both the water and wax which has been softened by the water. This effectively creates a closed system ensuring that only a minimal amount of fluid is left in the ear canal post-procedure.

In further modifications or adaptations, the ear examination tool 1 may include a three-dimension visualisation system to facilitate 3D visualisation of the ear canal and ear drum and thereby provide depth perception to assist safe manipulation of the microsuction cannula within the ear canal. Normally, stereoscopic visualisation of the inner ear is provided only by expensive, stationary, clinic-based stereomicroscopes. However, as described here, the ear examination tool 1 can be adapted to provide for stereoscopic viewing.

Figure 7:
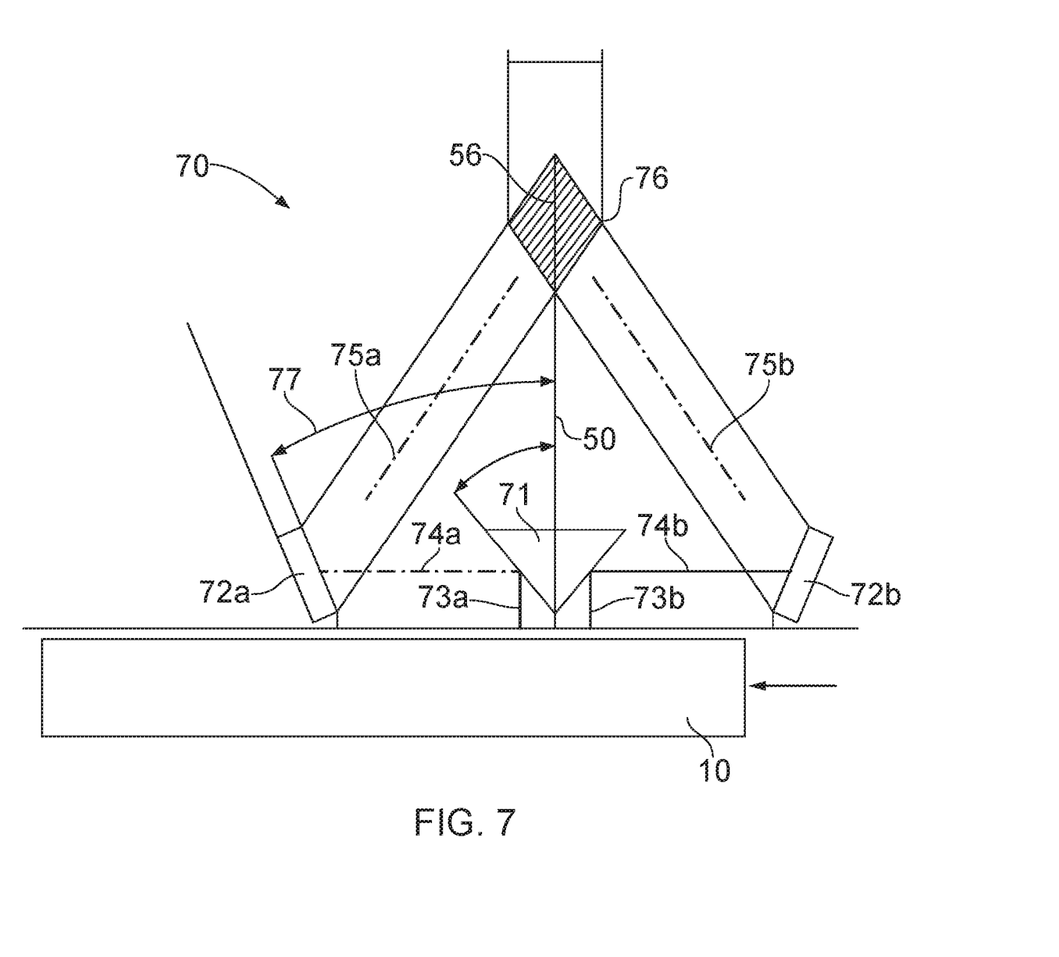
FIG. 7 shows a schematic plan view of a 3D optical element for use with the ear examination tool of FIG. 1 or FIG. 3.

With reference to FIG. 7, the optical aperture 12 positioned in front of the smartphone camera lens may comprise a 3D optical element. A 3D optical element 70 in this example comprises a prism 71 positioned on the cradle 9 in front of the camera of the smartphone 10 and has left and right outer mirrors 72a, 72b. The line of the first optical path 50 is indicated in FIG. 7 and bisects the prism 71, such that the prism 71 and outer mirrors 72a, 72b define left and right optical paths 73a, 73b respectively diverging to paths 74a, 74b and then converging with paths 75a, 75b, so as to converge at the intersection point 56 in a stereoscopic viewing region 76. The half baselines corresponding to paths 74a, 74b and the mirror angles (e.g. labelled 77 for the left pathway) may be adjustable to vary the position of the stereoscopic viewing region 76 or they may be fixed for a fixed examination tool geometry.

A suitable app may be loaded to the smartphone. An acquired stereo image may initially be formed on a single frame and a manual image dissection performed on the touch screen of the smartphone to distinguish the left and right image channels. Once the channels are separated, a stereo camera calibration method can be performed to determine the intrinsic and extrinsic values of the stereo camera system. This may be preconfigured by the app for a specific 3D optical element 70. When the stereo camera system parameters are known, the image pair can be undistorted and rectified to account for the lens, mirror and/or prism distortions and to account for the virtual baseline between the two virtual cameras. Digital magnification, exposure and sensitivity can be adjusted to best suit the surgical application. The left and right image feeds are thereby corrected and live video from the camera system can be interlaced so that a line-by-line stereo image can be seen by the operator. This can be performed on the smartphone, for example using FFMPEG libraries, OpenCV and Apple's AVFoundation API. The image processing allows a true 3D magnified, illuminated view of the inner ear on the smartphone display. The smartphone display screen 60 can be provided with a lenticular display cover, such as the EyeFly3D Nanoglass screen protector or other transparent cover that will provide a similar parallax barrier. Alternatively, the smartphone display could be configured to provide 3D images in conjunction with suitable 3D viewing spectacles for the user.

In some later generation smartphones, a dual camera for 3D stereoscopic viewing may already be built in. In this case, such functionality could be deployed without further optical elements being attached to the cradle 9/smartphone 10. Future systems might deploy plenoptic or light field cameras which might be integrated into smartphones.

The smartphone app may generally provide a number of other useful functionalities such as: magnification adjustments; lighting adjustments; focusing point adjustments; enlargement factor; image capture and storage which can include video capture of the procedure; addition of data to captured images such as patient data, time, date and user identification, to name but a few examples.

To further aid in ease of use of the ear examination tool 1, various smartphone functions and/or microsuction tool functions could be controlled by the user's hand that is gripping the handle 2. For this purpose, the handle 2 could be provided with one or more control trigger buttons on the handle. These could communicate with either the smartphone and/or the suction device using a suitable wireless communication channel, such as a Bluetooth connection, to implement one or more useful functions within the smartphone or suction device. Such functions could include altering focusing parameters, changing illumination levels, start/stop recording or image capture, start/stop irrigation and/or suction, etc.

In another modification, some functionality of the microsuction apparatus could be built in to the ear examination tool handle 2, such as a fluid reservoir for supplying fluid to the cannula 82 by way of the flexible delivery tube 88 coupled to the central lumen 84, for example.

In another example, illumination of the inner ear may be provided by illumination sources such as LEDs mounted on or integrated with the speculum mount.

The ear examination tool described herein provides a low cost device which harnesses the advanced functionality of many smartphones to provide a substantial improvement in the microsuction and ear examination functionality at a cost well below that of clinic- and hospital-based fixed equipment and enables the microsuction procedure to be performed in a much wider community setting.

Other embodiments are intentionally within the scope of the accompanying claims.

The invention claimed is:

1. An ear examination tool comprising:
   a handle;
   a spacing element coupled to the handle and extending from the handle, the spacing element having a distal end and a proximal end;
   a speculum mount coupled to the handle at the distal end of the spacing element, the speculum mount configured for retaining a speculum; and
   a smartphone mount coupled to the spacing element at the proximal end of the spacing element,
   the spacing element configured to maintain an optical separation distance between the speculum mount and the smartphone mount along a central axis of the speculum mount,
   wherein the speculum mount, the spacing element and the smartphone mount are configured to provide an optical path from the smartphone mount to and along the central axis of the speculum mount, while allowing a clear space for access by a microsuction device into and through a speculum when mounted to the speculum mount, from a position between the speculum mount and the smartphone mount and at an oblique angle to the optical path,
   in which the handle extends from the distal end of the spacing element in a direction generally orthogonal to the optical path, or in which the handle extends along the spacing element.

2. The ear examination tool of claim 1 in which the smartphone mount comprises a cradle configured to releasably receive and retain a smartphone,
   the cradle including at least one aperture therein positioned such that, when a smartphone is mounted in the cradle, the ear examination tool provides
   a first optical path extending from a first position of the smartphone mount corresponding to a smartphone camera to and along the central axis of the speculum mount, and
   a second optical path extending from a second position of the smartphone mount corresponding to a smartphone light source and oblique to the central axis of the speculum mount,
   the first and second optical paths intersecting at a point distal of the speculum mount.

3. The ear examination tool of claim 1 in which the speculum mount comprises an aperture extending therethrough and a receptacle on a distal side of the speculum mount for attachment of a speculum.

4. The ear examination tool of claim 1 in which the handle extends in the direction generally orthogonal to the optical path and in which the handle is positioned less than 3 cm from a distal side of the speculum mount along the central axis.

5. The ear examination tool of claim 1 in which the smartphone mount further comprises an optical element configured, in use, to be positioned over a camera of a smartphone when installed in the smartphone mount.

6. The ear examination tool of claim 5 in which the optical element comprises a stereoscopic vision element configured to provide dual images to a smartphone camera when the smartphone is installed in the smartphone mount.

7. The ear examination tool of claim 1 in which the smartphone mount further comprises an optical element configured, in use, to be positioned over a light source of a smartphone when installed in the smartphone mount.

8. The ear examination tool of claim 1 in which the smartphone mount is adaptable to fit a plurality of different types of smartphone.

9. The ear examination tool of claim 1 further comprising a plurality of interchangeable smartphone mounts each configured to fit a different type of smartphone and each separately couplable to the spacing element.

10. The ear examination tool of claim 1 in which the handle incorporates a fluid reservoir for supplying fluid to an ear suction apparatus.

11. The ear examination tool of claim 1 in which the handle comprises a control trigger to implement a function in an associated suction device or an associated smartphone.

* * * * *